United States Patent [19]
Haynes

[11] Patent Number: 5,486,163
[45] Date of Patent: Jan. 23, 1996

[54] PROTECTIVE SHIELD FOR HYPODERMIC SYRINGE

[75] Inventor: Don A. Haynes, Okemos, Mich.

[73] Assignee: Haynes-Miller, Inc., Okemos, Mich.

[21] Appl. No.: 243,562

[22] Filed: May 16, 1994

Related U.S. Application Data

[63] Continuation-in-part of Ser. No. 65,807, May 21, 1993, Pat. No. 5,312,368.

[51] Int. Cl.⁶ .................................................. A61M 5/32
[52] U.S. Cl. ............................................ 604/192; 604/263
[58] Field of Search ................................. 604/192, 198, 604/187, 263, 110

[56] References Cited

U.S. PATENT DOCUMENTS

| | | | |
|---|---|---|---|
| 4,664,259 | 5/1987 | Landis | 604/192 |
| 4,929,241 | 5/1990 | Kulli | 604/263 |
| 4,935,013 | 6/1990 | Haber et al. | 604/192 |
| 4,950,249 | 8/1990 | Jagger et al. | 604/192 |
| 4,950,250 | 8/1990 | Haber et al. | 604/192 |
| 4,966,591 | 10/1990 | Yuen | 604/192 |
| 4,976,699 | 12/1990 | Gold | 604/192 |
| 5,011,479 | 4/1991 | Le et al. | 604/198 |
| 5,017,189 | 5/1991 | Boumendil | 604/263 X |
| 5,055,102 | 10/1991 | Sitnik | 604/192 |
| 5,059,180 | 10/1991 | McLees | 604/110 |
| 5,078,697 | 1/1992 | Rammler | 604/198 |
| 5,135,509 | 8/1992 | Olliffe | 604/192 |
| 5,167,649 | 12/1992 | Balding | 604/192 |
| 5,171,303 | 12/1992 | DeCamp | 604/192 |
| 5,232,455 | 8/1993 | Hollister | 604/263 |
| 5,242,417 | 9/1993 | Paudler | 604/263 X |
| 5,312,369 | 5/1994 | Arcusin et al. | 604/192 |

FOREIGN PATENT DOCUMENTS

| | | | |
|---|---|---|---|
| 2618685 | 2/1989 | France | 604/192 |

*Primary Examiner*—John D. Yasko
*Attorney, Agent, or Firm*—Howard & Howard

[57] ABSTRACT

A shield for protecting the needle of a syringe. The shield has a connector for connecting the shield to the syringe with the connector preferably being generally annular and adapted to slip fit over the base of the needle, unless the syringe is formed with a needle, then the connector body would fit over the end of the syringe. The shield includes at least one protective arm hingedly mounted upon the connector and pivotable between first and second positions. The first position is the normal position wherein the protective arm conceals the needle and the second position corresponds to the protective arm being pivotally displaced to expose the needle. The arm is automatically biased to the first position so that the needle is normally and automatically concealed.

52 Claims, 7 Drawing Sheets

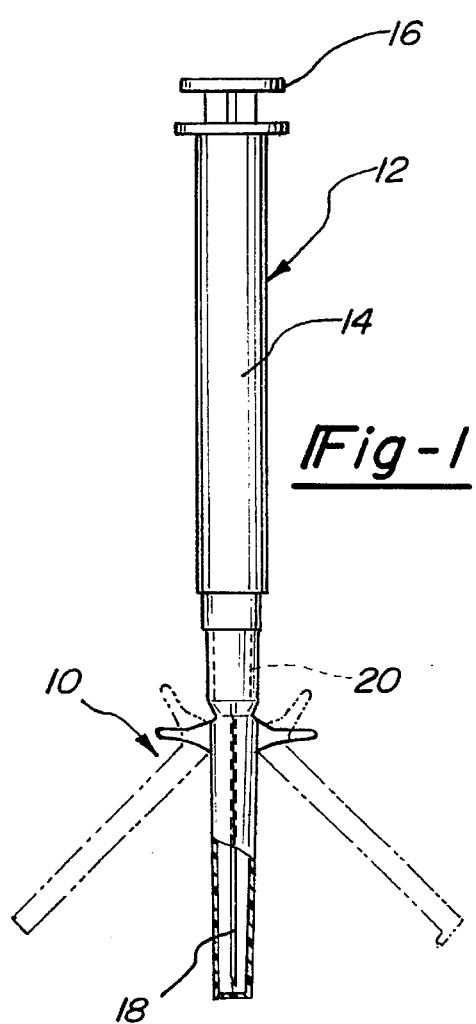
Fig-1
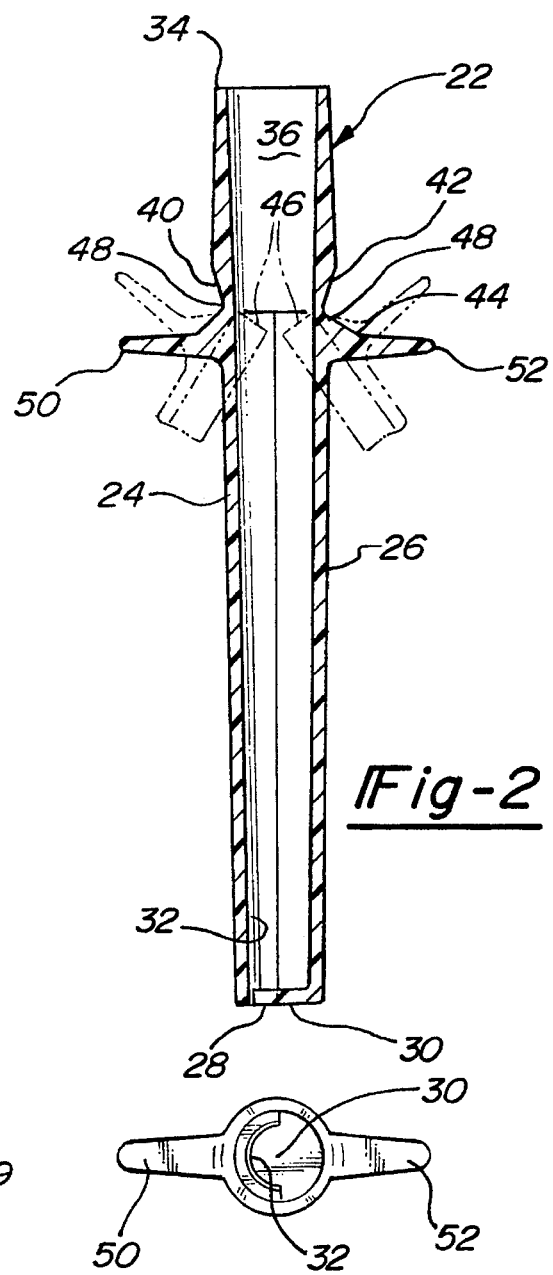
Fig-2
Fig-2A
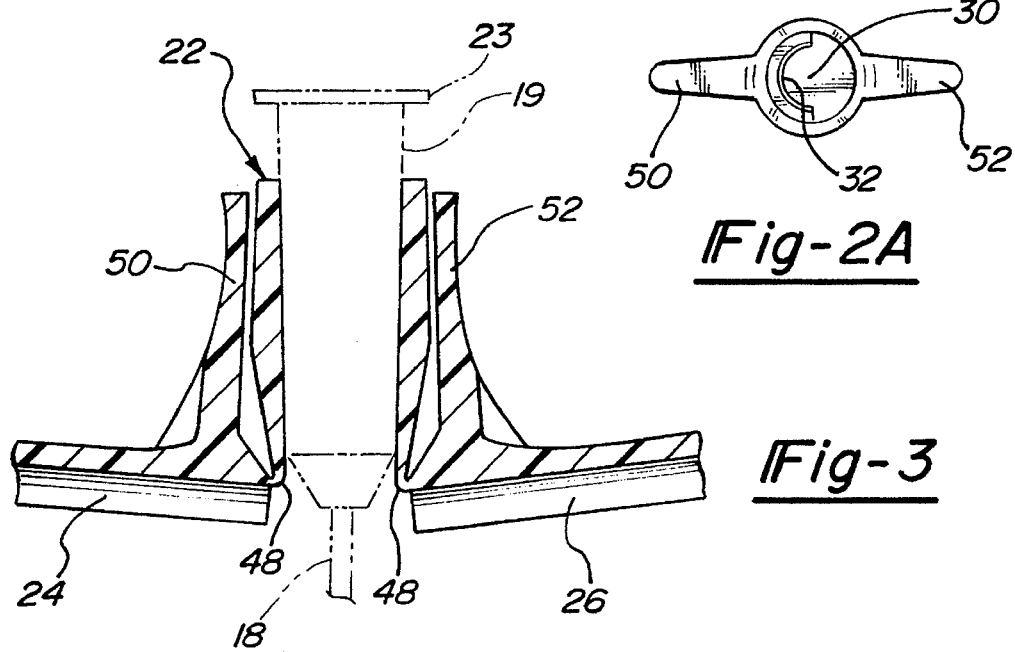
Fig-3

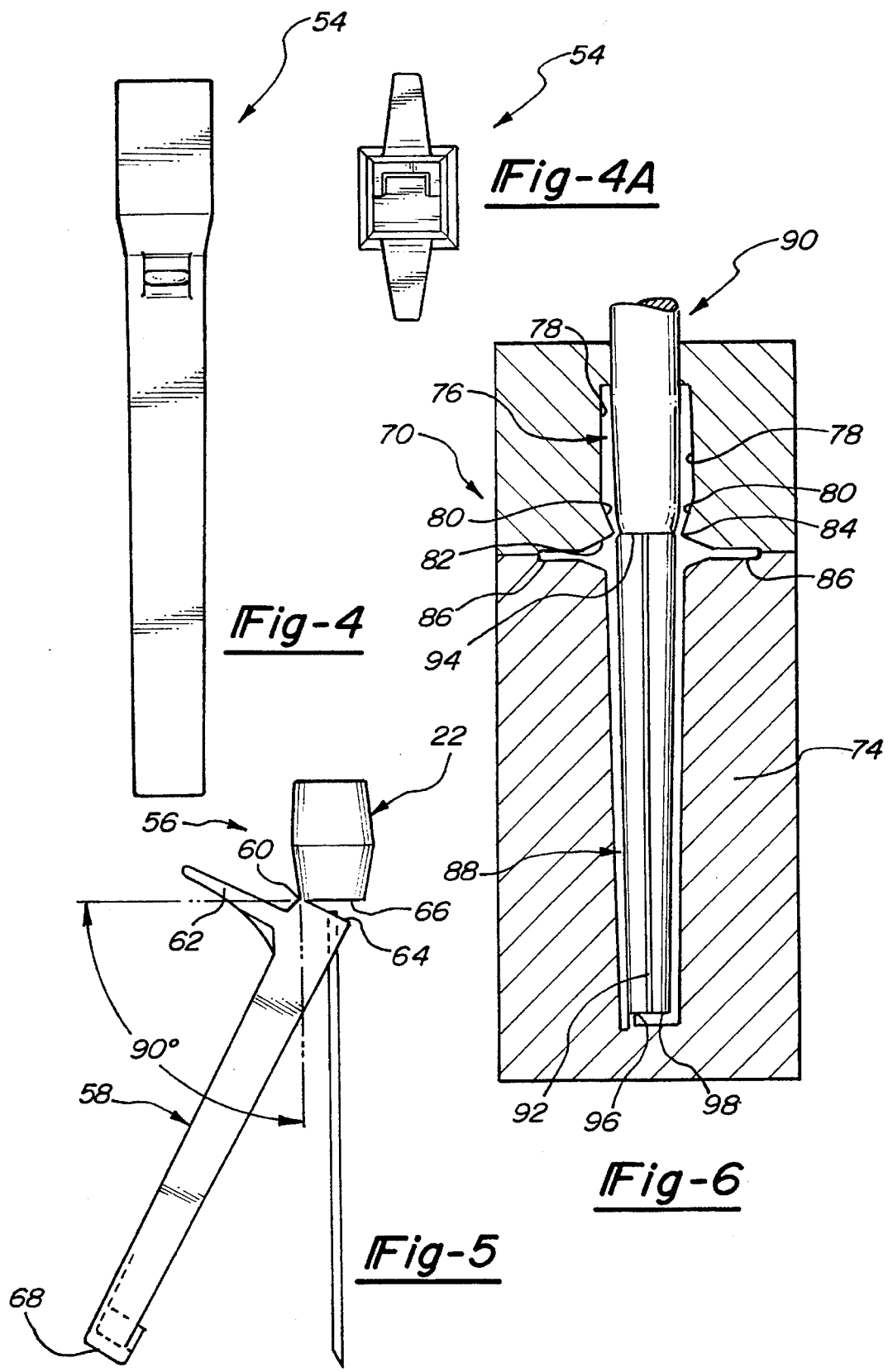

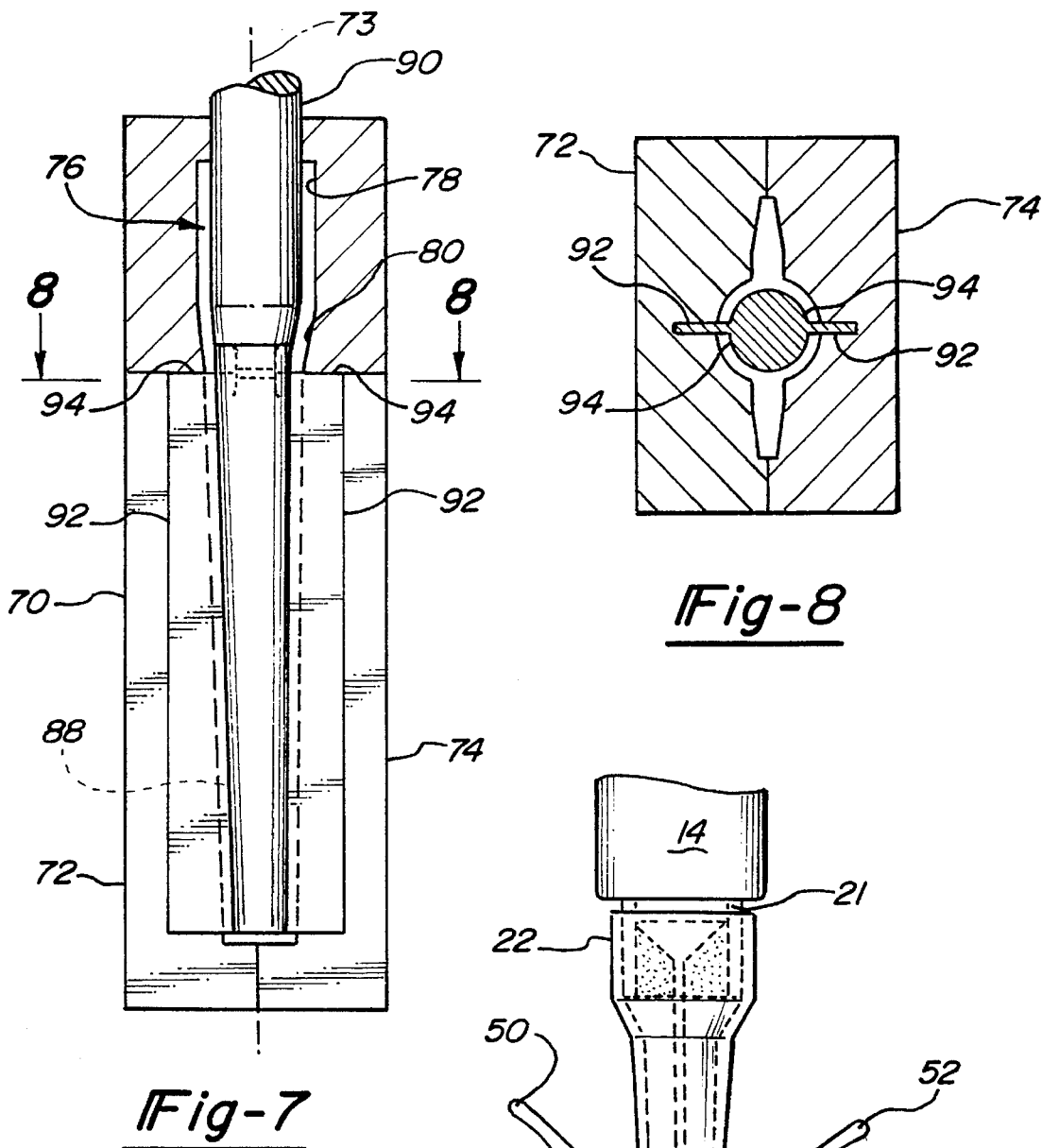
Fig-7
Fig-8
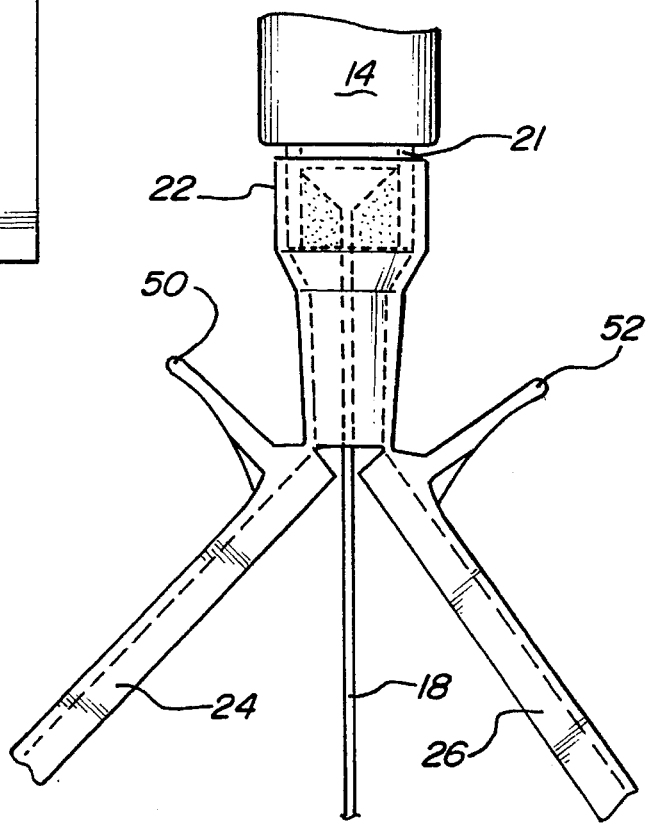
Fig-9

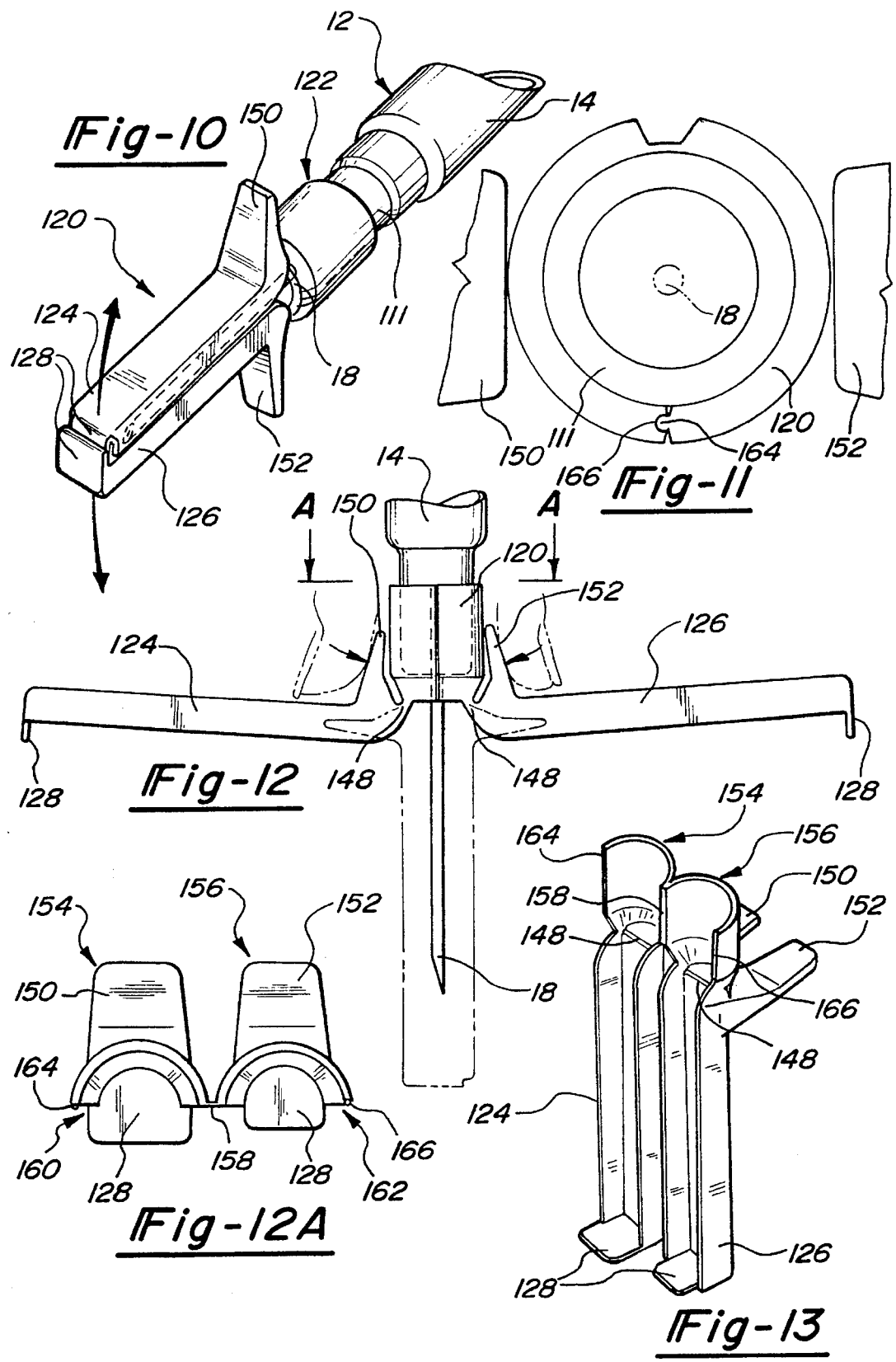

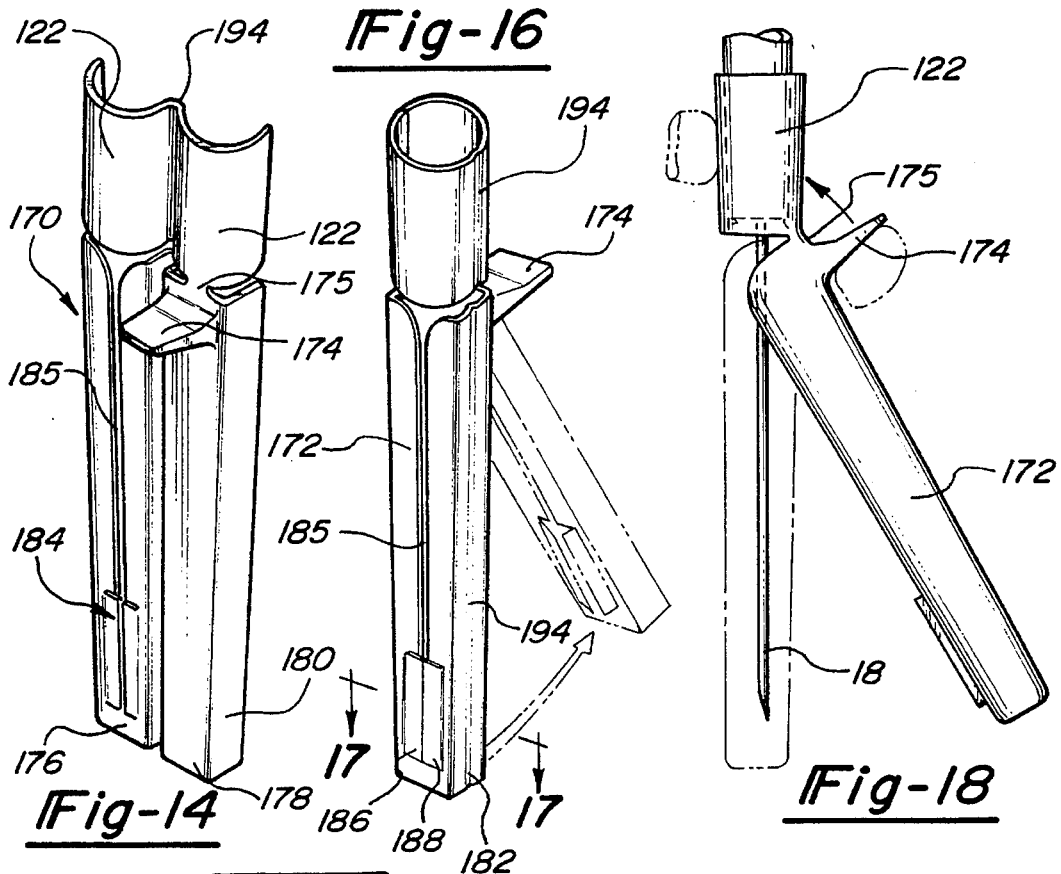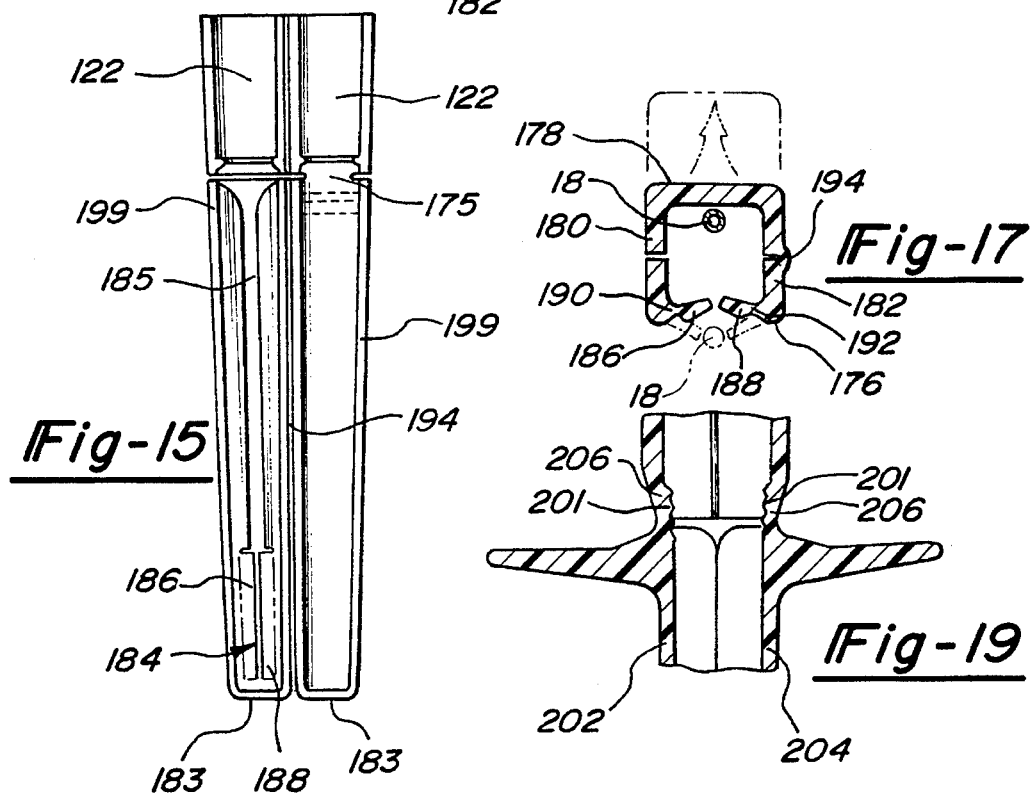

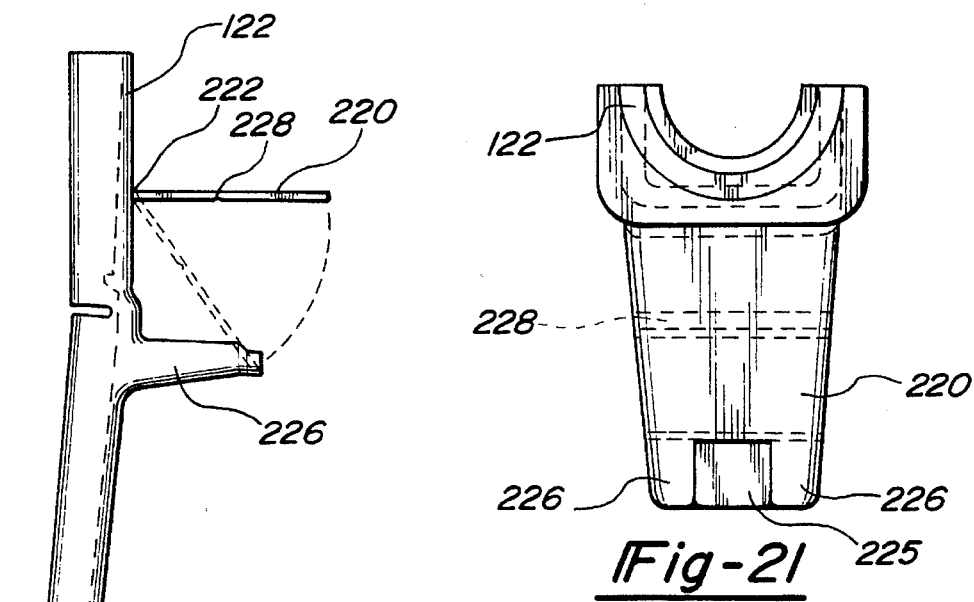
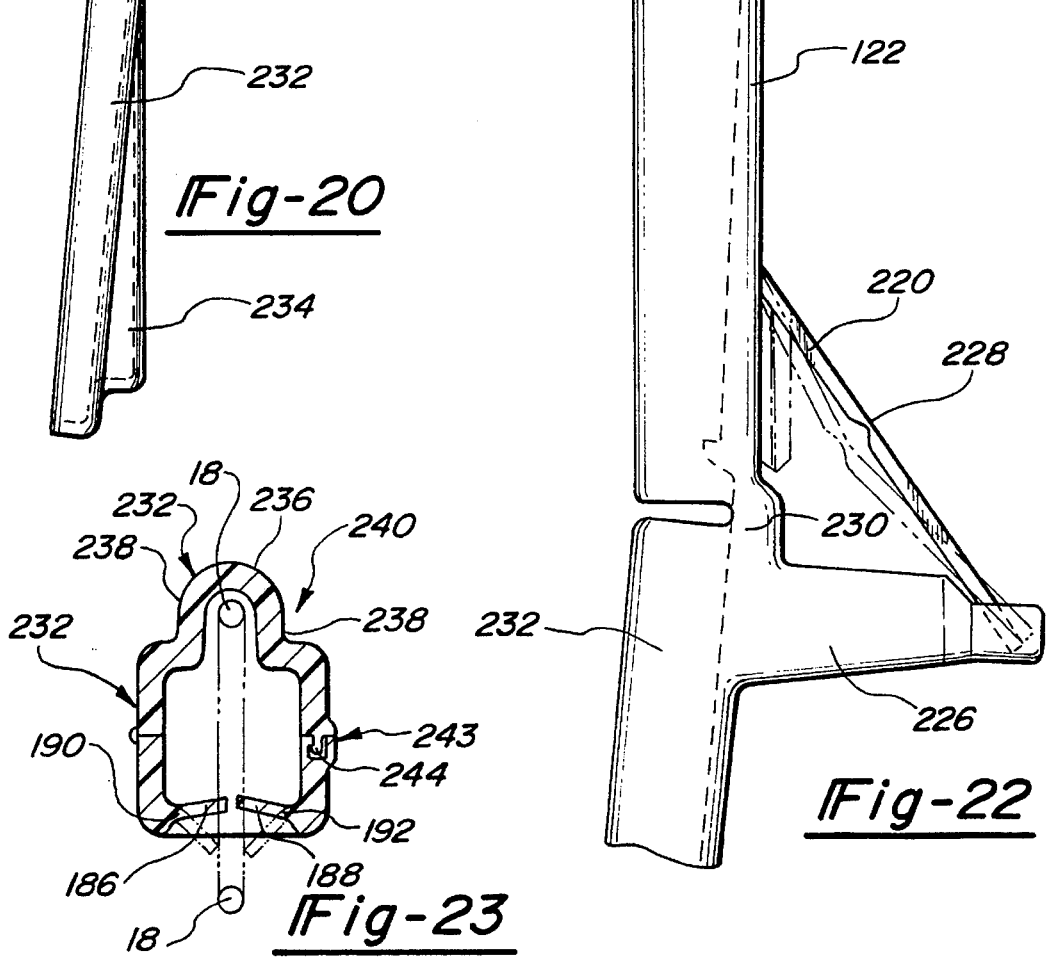

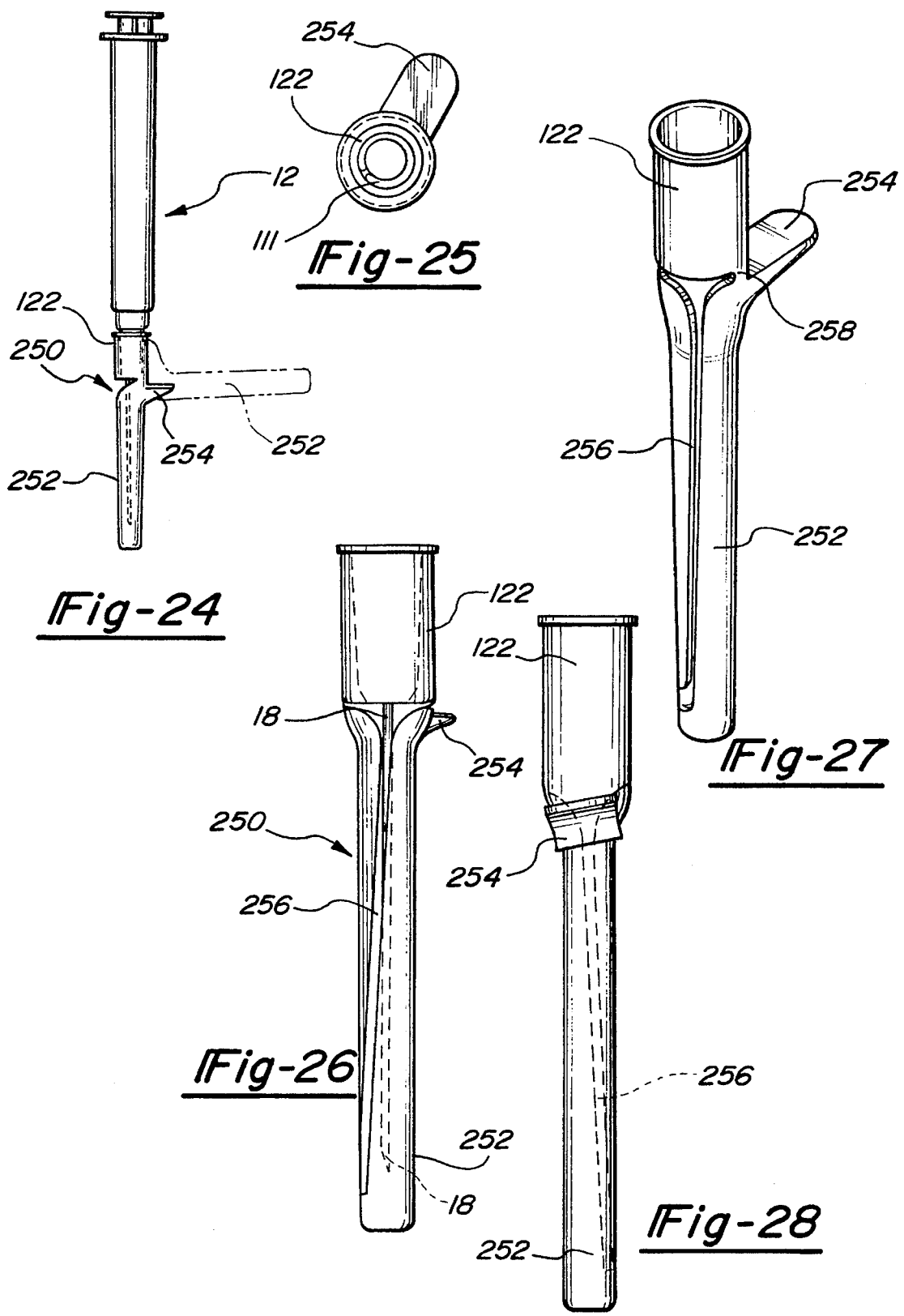

PROTECTIVE SHIELD FOR HYPODERMIC SYRINGE

This is a continuation-in-part of application Ser. No. 08/065,807, filed on May 21, 1993 now U.S. Pat. No. 5,312,368.

BACKGROUND OF THE INVENTION

The present invention relates to a protective device for a hypodermic syringe and more importantly to a protective device that normally and automatically envelopes the needle of a hypodermic syringe.

There have been many attempts to make protective devices to protect users of hypodermic syringes from inadvertent punctures. This has become a particular concern now with the consequences of AIDS. To Applicant's knowledge, these prior attempts have all been attempts to conceal the needle during transport, either before or after use. The known devices typically require manual movement of a sheath or similar protective member to expose the needle so that the needle can be used and once an injection is made, manual movement of the sheath to conceal the needle so that the needle can be disposed of without inadvertent puncture.

These known sheaths do not address the danger of an exposed needle during the period just prior to use through just after the injection during which the sheath does not conceal the needle. For example, there is the possibility that during the injection the patient will jump and the needle will be dropped or it may be propelled into the air. The Applicant is aware of instances where the needle has been propelled and inadvertently stuck the individual giving the injection.

The only protective sheaths that the Applicant is aware of that provide protection during the period of use employ a coil spring to automatically extend the sheath. These protective sheaths either require too much manipulation or are too costly.

SUMMARY OF THE INVENTION

The protective devise of the present invention overcomes the above problems found in known devices by providing an inexpensive automatic shield that normally conceals the needle of a hypodermic syringe and has to be manually biased to expose the needle.

The protective shield of the preferred embodiment of the present invention is a clam shell type design having two members that are normally closed about the needle of the syringe. The shield includes a mounting collar that is preferably slip fit over the end of the base of the needle or syringe body. The two members are hingedly connected to the mounting collar so that they can pivot with respect to the needle. In order to expose the needle, the two members are pivoted about the hinge with respect to one another. In the disclosed embodiment, there are finger grips provided to facilitate the pivoting of the two members. The hinge is formed so that it biases against the members, biasing them back to the normal position corresponding to the closed position. In this way, due to the bias, the two members are automatically returned to the concealing position if the manual applied force on the members is released, as for example if the needle and syringe is dropped or knocked from the user's hand.

As should be appreciated by one of ordinary skill in the art, the sheath would not need to be removed from the needle for use which greatly reduces the potential for contamination. Further, as soon as the needle is inserted, the force to open the sheath can be released and the two halves of the sheath, because of the resilient memory of the material used, will automatically close the two halves against the skin of the patient. Since there are only a few ounces of force needed to close the two members, the patient feels no discomfort. When the needle is removed, by purpose or accident, the sheath snaps shut, covering the needle.

The present application also discloses an alternative embodiment of the present invention wherein there is only one pivotal member that has an open side for exposing the needle. The one member or arm is pivoted against the bias of the hinge in a manner similar to the above clam-type shield.

This application also discloses further embodiments, including added means for protecting against inadvertent opening of the protective arms. These means take the form of a protective door and a locking brace. Still further, there is a pocket disclosed for added concealment of the needle.

There is also disclosed various methods for making the shield of the present invention.

BRIEF DESCRIPTION OF THE DRAWINGS

FIG. 1 is a plan view of the protective shield of the present invention mounted upon the base of the needle attached to a hypodermic syringe.

FIG. 2 is a plan view of the protective shield of the present invention.

FIG. $2^A$ is an end view of the preferred embodiment of the present invention.

FIG. 3 is a plan view of the protective shield attached to the base of the needle of the present invention in the exposed position.

FIG. 4 is a side view of a second embodiment of the present invention.

FIG. $4^A$ is an end view of the shield illustrated in FIG. 4.

FIG. 5 is a further embodiment of the shield of the present invention.

FIG. 6 is a top view of the preferred mold for injection molding the shield of the present invention with the top of the mold removed.

FIG. 7 is a cut away side view of the preferred mold for injection molding of the shield.

FIG. 8 is a view taken along line 8—8 of FIG. 7.

FIG. 9 is a view of the protective shield mounted to the end portion of a hypodermic syringe.

FIG. 10 is a perspective view of a further embodiment of the shield of the present invention.

FIG. 11 is a cross-section taken along line A—A of FIG. 12.

FIG. 12 is a plan view of the embodiment of FIG. 10.

FIG. $12^A$ is a top view of the embodiment of FIG. 10 with the two halves of the needle shield open.

FIG. 13 is a perspective view of FIG. $12^A$.

FIG. 14 is a perspective view of a further embodiment of the shield of the present invention with the disclosed two halves open.

FIG. 15 is a plan view of FIG. 14.

FIG. 16 is a perspective view of the shield of FIG. 14, with the two halves joined and illustrating the movement of the protective arm.

FIG. 17 is a cross-section taken along line 17—17 of FIG. 16.

FIG. 18 is a side view of FIG. 16.

FIG. 19 is a partial cross-section of a further embodiment of the sheath of the present invention.

FIG. 20 is a partial plan view of a still further embodiment of the present invention.

FIG. 21 is a partial top view of the connector body and finger grip of the shield illustrated in FIG. 20.

FIG. 22 is a partial view of FIG. 20.

FIG. 23 is a cross-section taken along line 23—23 of FIG. 20.

FIG. 24 is a side view of a syringe with a further embodiment of the present invention attached.

FIG. 25 is a top view of the sheath illustrated in FIG. 24.

FIG. 26 is a side view of the shield of FIG. 24.

FIG. 27 is a front perspective view of the shield of FIG. 24.

FIG. 28 is a rear view of the shield of FIG. 24.

DETAILED DESCRIPTION OF THE PREFERRED EMBODIMENT

The protective hypodermic needle shield of the present invention is shown generally at 10 in FIG. 1. The shield 10 is mounted upon the base 19 of needle 18 on a standard hypodermic syringe 12 (see FIG. 3). The syringe 12 includes a barrel 14 which receives a plunger 16 at one end and has a hypodermic needle 18 attached at the opposite end. It is to be understood that syringe as used in this application, refers broadly to the barrel, needle and base of needle, and any hub or end portion of the barrel. The disclosed hypodermic syringe includes a coupling 20 that couples the base 19 of needle 18 to the barrel 14. The coupling 20 allows the needle 18 to be removed from barrel 14. It should be understood that the needle 18 could be integrally formed to the barrel 14 without affecting the application of the present invention. It is also within the scope of this invention that the protective shield 10 can be mounted to the end of the syringe 12 adjacent to the needle 18 or mounted to the barrel 14 of the syringe 12.

With reference to FIG. 2, the shield 10 of the present invention is shown in greater detail. The shield 10 has a connector body 22 which slide on the base 19 of the needle 18. The shield is generally installed on the needle at the time of assembly. With reference to FIG. 3, Luer-Lok tabs 23 are illustrated for example as a known method of attaching the needle 18 to barrel 14. Tabs 23 molded are into base 19 of needle 18 onto which the connector body 22 slides. The vertical projections normally found on the base 19 of the needle are not illustrated, but those of ordinary skill in the art will appreciate that these projections are received within grooves to receive the projections to prevent slipping. Syringes with a slip-tip would not require the grooves. As should be appreciated, other methods of preventing the sheath of the present invention from slipping will become apparent to those of ordinary skill in the art and are considered to be within the scope of this invention.

As illustrated in FIG. 2, the protective arms 24 and 26 each have a semicircular cross-section. The arms 24 and 26 are illustrated in the closed position wherein the arms mate to form a circular cross-section with a closed end 30 to envelope the needle 18. The closed position is the normal position for the arms 24 and 26 so that the needle 18 normally remains enveloped preventing inadvertent puncture by the needle 18.

The sheath is generally tubular in shape and has a slight taper from its top 34 to end portion 30. The inner diameter 36 of connector body 22 is made to fit the outer diameter of the base 19 of needle 18, or the end portion 21 of the barrel 14 if there is no coupling 20 or the barrel 14 if it is desired to mount shield 10 to the barrel 14. This permits the connector body 22 to be slip fit onto syringe 12.

As disclosed, the arm 24 terminates in an end face 28. The arm 26 terminates in an inwardly turned end portion 30 that abuts against the inner wall 32 of arm 24 to cover the terminal end of the needle 18. In this way, the needle is fully enclosed.

As stated above, the arms 24 and 26 are normally in the closed position as illustrated by the solid lines in FIG. 2. To expose the needle 18, the arms 24 and 26 must be pivoted with respect to the syringe 12. The pivoting action is shown by the phantom lines in FIG. 1 and 2. In order for the arms 24 and 26 to pivot, the sheath has a reduced outer diameter at 40. In the embodiment illustrated in FIGS. 1 and 2, the reduced diameter is defined by intersecting angled walls 42 and 44 which intersect at the top 46 of the arms 24 and 26.

The reduced diameter 40 defines flexible hinges 48 between the arms 24 and 26 and the connector 22 which bias arms 24 and 26 to their closed position to conceal the needle 18. Protruding outwardly from the arms 24 and 26 are finger grips 50 and 52. In the preferred embodiment of the invention, the finger grips 50 and 52 are integrally formed with the remainder of the shield 10. As illustrated in FIGS. 1 and 2, the top of the finger grips define the angled wall 44 of reduced portion 40.

With reference to FIG. 3, the fully open position of sheath 10 is illustrated. The arms 24 and 26 are generally perpendicular to the syringe 12 fully exposing the needle 18. In this position the fingers 50 and 52 are pressed by the user against the connector body 22. It should be understood that the hinges 48 are biasing the arms 24 and 26 to the normally closed position as shown in FIGS. 1 and 2. The user is responsible for holding the arms 24 and 26 in the illustrated position to expose the needle 18. If the user releases the fingers 50 and 52 the arms 24 and 26 will automatically be forced back to the closed position concealing the needle 18. To facilitate the users ability to hold the arms 24 and 26, finger grips 50 and 52 are slightly concave to conform to the user's finger and thumb. Knurling can also be used to facilitate gripping.

With reference to FIG. 4, a further embodiment of the shield 10 of the present invention is shown generally at 54. This embodiment is generally the same as the previous embodiment, except that it has a square cross-section, see FIG. $4^A$ as opposed to a circular cross-section, see FIG. $2^A$. It should be understood by those of ordinary skill in the art that the cross-section could have other geometric shapes, for example it could have a triangular cross-section with the arm 24 being generally flat in cross-section and the arm 26 having a triangular cross-section.

With reference to FIG. 5, another embodiment of the shield of the present invention is shown generally at 56. As before, the shield 56 has a connector body 22 for a slip fit connection to the base 19 of needle 18. In this embodiment, instead of two arms 24 and 26, there is a single arm 58 which is hinged at 60 to connector body 22. One side of arm 58 has an opening wide enough to let the needle 18 pass through during movement. A single finger 62 is used to pivot the arm 58 from the normally closed position, in which the needle 18 is covered, to the fully exposed position, in which the needle is fully exposed. The arm 58 is generally perpendicular to the needle 18 in the fully exposed position. As before, the hinge 60 resists efforts to pivot the arm 58 from the normally closed position, i.e. generally parallel to the needle 18, to the fully exposed position, i.e. generally perpendicular to needle 18.

As can be appreciated, the arm 58 will automatically return to the closed position. In this embodiment the top 64 of arm 58 extends across the base 66 of connector 22. In the previous embodiment, the tops 46 of each arm 24 and 26 extended only about one-half the distance across the base of the connector 22. Additionally, in this embodiment the end 68 extends at a generally right angle with respect to the arm 58 to cover the end of needle 18 when the arm is in the closed position.

With reference to FIG. 6, a preferred mold and method of making the sheath 10 of the present invention will be described. The mold is shown generally at 70. The mold has two halves, a top half 72 and a bottom half 74 that can be separated along a longitudinally extending part line 73. The mold halves 72 and 74 form cavities which define the exterior of the sheath 10. The cavity 76, formed by the two molds 72 and 74, has a first inside diameter 78 that tapers slightly to an inwardly angled portion 80 that corresponds to wall 42. The inwardly angled portion 80 ends at an apex 84 which begins the outwardly angled portion 82 that corresponds to the wall 44. The angled portion 82 extends to a generally perpendicular cavity 86 relative to the center line that defines the fingers 50 and 52. The perpendicular cavity 86 is formed on both the top half 72 and bottom half 74 of the mold 70. Extending into the top half 72 and the bottom half 74 is a tapered cavity 88 that defines the outer surface of the arms 24 and 26.

A core insert 90 is adapted to be inserted into the cavities 72 and 74. Core insert 90 defines the interior of the sheath 10. The insert 90 is slightly tapered along its length. To define the two arms 24 and 26, longitudinal blades 92 are inserted project in from the molds 72 and 74 on opposed sides of the insert 90. The blades 92 extend in to the insert 90, which has shallow grooves to accept them. As should be appreciated, the blades will form a line of separation on both sides of the arms 24 and 26 when they are molded. A second pair of smaller blades 94 are inserted or projected in from the molds 72 and 74, which are generally perpendicular to the blades 92. It should be appreciated that the blades 94 will have an interior shape that is the same as the exterior shape of core insert 90. The blades 94 define the tops 46 of the arms 24 and 26.

In the preferred embodiment, blades 94 are inserted in grooves cut in the top half 72 and bottom half 74. Also, blades 92 are inserted in grooves cut in the top half 72 and bottom half 74. The blades 92 abut blades 94 when closed. Shallow grooves are cut in insert 90 to accept the blades 92 and 94 when closed. With insert 90 in place to mold sheath 10, the top 72 and bottom 74 of the mold 70 are connected together by means well known to those of ordinary skill in the art. An engineered material is then injected into the cavity to form sheath 10. Once the material has obtained the shape of the cavity and sets, molds 72 and 74 are separated to enable the sheath 10 to be removed. It should be appreciated that the material to be used for the sheath 10 will require the necessary physical and mechanical properties such that the needle will automatically be protected by arms 24 and 26 after release of fingers 50 and 52 which control exposure of needle 18. It is believed that a plastic such as polypropylene will be acceptable, but it is believed that other spring type material would be acceptable.

It should be understood that the other embodiments could be molded in a similar mold with slight variations to the mold. The mold of the preferred embodiment permits sheaths to be quickly and inexpensively molded.

With reference to FIG. 10, a further embodiment of the present invention is illustrated at 120. Sheath 120 includes a connector body 122 for connecting the sheath 120 to a syringe 12. It should be understood that connector body 122 can be dimensioned to connect the sheath 120 to the end 111 of the syringe 12 as illustrated or to the body 14, or to the needle 18, or to the coupling 20 as shown in FIG. 1. It should be further appreciated by those of ordinary skill in the art that the inside diameter and, if desired, the outside diameter of the connector body 122 would be appropriately dimensioned to facilitate mounting of the connector body 122 to the desired location.

Extending from the connector body 122 are protective arms 124 and 126, which include a pair of end faces 128. As previously described, the end faces 128 conceal the end of needle 18 to prevent inadvertent punctures. As in the previous embodiment, fingers 150 and 152 are provided to permit manipulation of the protective arms 124 and 126 from the closed position shown in FIG. 10 to the open position shown in FIG. 12. In FIG. 12, a user's fingers are shown pressing against fingers 150 and 152, holding the protective arms 124 and 126 in the open position. In the disclosed embodiment, the arms 124 and 126 are integrally formed with connector body 122, with a resilient hinge or stress member 148 joining them. The hinge 148 is sufficiently resilient to force against the protective arms 124 and 126 to spring them from the open position shown in FIG. 12 to the normally closed position shown in FIG. 10.

With reference to FIG. 12$^A$ and FIG. 13, the sheath 120 is illustrated as two nearly identical halves shown generally at 154 and 156 which can be folded about a resilient portion 158 to form the sheath 120 as illustrated in FIG. 10. The resilient portion 158 is illustrated extending the length of the connector body 120 (see FIG. 13). It should be appreciated that portion 158 could be much shorter and still connect the halves 154 and 156. It is within the scope of the invention to not even provide portion 158 altogether. If excluded, the two halves would then need to be joined along the four free edges as opposed to the two free edges 160 and 162. Although the Applicant does not believe it would be as desirable, it would still function properly.

The free edges 160 and 162 of the connector body 120, as illustrated in FIGS. 12$^A$ and 13, include a locking means for locking the two halves 154 and 152 together. In the disclosed embodiment, the locking means is a male protrusion 164 and a female opening 166. The female opening 166 has a reduced diameter opening such that the male protrusion 164 can be snapped into it and retained. In the disclosed embodiment, the male protrusion 164 extends the length of the free edge 160, and the female opening 166 extends the length of free edge 162. It should be appreciated that the length of the locking means could be much less, or in the alternative, more than one male protrusion 164 and female opening 166 could be used. In use, the two halves 154 and 156 can be folded over portion 158, and the male protrusion 164 snapped into female opening 166 to lock the two halves together. Once the two halves are snapped together, the connector body 122 is formed and can be slipped over the syringe 12.

Additional locking means could be used. For example, the locking means could be an adhesive to adhere the free edges 160 and 162 together. Another method to lock the connector body 122 together would be to use a shrink wrap material to shrink about the connector body 122 and lock the free edges 160 and 162 together.

With reference to FIG. 14, a further embodiment of the sheath of the present invention is illustrated generally at 170. As in the previous embodiment, the sheath 170 is formed in two halves.

In the illustrated embodiment, the sheath 170 has a single protective arm 172 and a single finger 174. The protective arm 172 is interconnected to the connector body 122 by a resilient hinge or stress member 175.

As can be seen in FIG. 18, the single protective arm 172 can be rotated to expose the needle 18 by grasping the syringe, preferably at the connector body 122 and the finger 174 and thereafter squeeze the finger 174 against the connector body 122. The movement of the protective arm 172 is illustrated in FIGS. 16 and 18.

The sheath 170 is illustrated with four sides—176, 178, 180, 182, and a bottom 183. The side 176 has a slot 185 for ingress and egress of the needle 18. As should be appreciated, the slot 185 is slightly wider than the maximum diameter of needle 18 to allow free movement of the sheath 170 about needle 18. This configuration of sheath 170 completely encompasses the needle in the normally closed position to prevent inadvertent punctures. As in all the previous embodiments, the protective arm 172 is normally in the position shown in solid lines in FIG. 16 and must be biased against stress member 175 to the position illustrated in phantom lines in FIG. 16. Stress member 175 will normally bias and force protective arm 172 back to the normal closed position.

To provide additional protection, the protective arm 172 includes an entrapment door 184 to resist movement of the protective arm 170 from the closed position to the open position. The entrapment door 184 is illustrated with two doors 186 and 188. The doors are approximately .015 inches in thickness and are secured to the side 176 by resilient hinges or stress points 190 and 192.

As illustrated in FIG. 17, the doors 186 and 188 are normally biased inwardly and in the preferred embodiment, at about 10 degrees to the side 176. The resilient hinges or stress points 190 and 192 allow the doors 186 and 188 to open as a result of the force of the needle 18 acting on the doors 186 and 188 as protective arm 172 is urged to the open position. The inward angle of the doors results in the need for very little force to open the doors 186 and 188 inwardly, to allow the protective arm to conceal needle 18, but results in the need for much greater force to expose the needle 18. In this way, the protective arm 172 is urged by little relative force to the normal closed position, and the doors 186 and 188 do not interfere with the protective arm 172 returning to the normally closed position about needle 18. However, the force required to open the doors, due to the bias, is a greater relative force to present inadvertent exposure of the needle 18.

As can be seen in FIGS. 14 and 15, the sheath 170 is formed in two halves which are joined along line 194. In the preferred embodiment, the connector body 122 is joined along line 194, and the protective arm is joined along line 194 by a stress point or living hinge. In this way, the two halves can be folded along line 194, and the free edges 199 connected to form the protective sheath 170, as illustrated in FIG. 1. The free edges can be attached in the same manner as the free edges of protective sheath 120. It should be appreciated that in this embodiment, the free edges 199 could be joined either along the connector body 122, the protective sheath 172, or both.

With reference to FIG. 19, a further embodiment of a resilient hinge 200 is illustrated. It is within the intended scope of the present invention that the hinge 200 could be used in any one of the various embodiments of the present invention. The hinge 200 includes a plurality of ridges and grooves that facilitate the ability to move the protective arms 202 and 204 from the normal closed position to the open position. Additionally, the hinge 200 facilitates the rapid return or snapping back of the protective arms 202 and 204. The ridges and grooves allow for a thicker area to increase the snap back at the hinge 200 without increasing the resistance to movement of the protective arms 202 and 204 to the open position.

With reference to FIGS. 20 through 22, a further method for locking the protective arm in the closed position is illustrated. In this embodiment, an articulated locking bar 220 is illustrated. In the preferred embodiment, the articulated locking bar 220 is integrally joined at 222 to the connector body 122. The bar 220 is illustrated having an opening 224, which is interference fit to a tab on the finger 226. It should be appreciated that bar 220 could be integrally joined to finger 226 instead of being interference fit. The bar 220 includes a hinge 228, allowing the bar to articulate. In the preferred embodiment, the hinge 228 is formed by forming a slot wedge-shaped recess in the bar 220. As can be seen in FIG. 22, the bar can be folded against the connector body 122 as the finger 226 is urged against connector body 122. This is illustrated by the phantom lines. In the normal position, the bar 220 is fully extended as illustrated by the solid lines.

In operation, the user presses inwardly against the hinge 228 to bend the bar 220 inwardly, while simultaneously pressing finger 226 in the direction of connector body 122. In the alternative, the bar 220 could be connected to finger grip 226 so that movement of finger 226 toward connector body 122 will automatically bend bar 220 at hinge 228 so that hinge 228 does not have to be pressed. As shown in phantom lines in FIG. 22, the bar 220 folds in half against the connector body 122. As long as the finger 226 is held by the user against the living resilient hinge 230, the needle remains exposed. Upon releasing pressure on finger 226, the living resilient hinge 230 will cause the protective arm 232 to snap back to its normally closed position, concealing the needle 18. In addition, the bar 220 is preloaded due to its being folded against living resilient hinge 228 and will provide additional force to the protective arm 232 to force it back to the bar's normal closed position. When fully extended, as shown in FIG. 22, the locking bar 220 acts as a lock to lock the protective arm 232 in its normally closed position.

With reference to FIG. 20, a pocket 234 is provided on the protective arm 232. As those of ordinary skill in the art will appreciate, the pocket could be used on any of the foregoing embodiments and, in particular, on the single arm sheaths. In the preferred embodiment, the pocket 234 has a back wall 236 and side walls 238. The back 236 and walls 238 are inclined outwardly from about midway on the side 240 of the protective arm 232 to about the end 242 of the protective arm 232. The pocket 234 receives the needle 18, allowing the protective arm 232 to be inclined at approximately 5 degrees with respect to the longitudinal center line of the needle 18. Depending on the depth and inclination of the pocket 234, various inclinations of the protective arm 232 can be obtained.

One advantage of the pocket 234 is the additional concealment of the needle 18. An additional advantage is the ability to preload the resilient hinge 230 to the normally closed position. The preloading of the hinge 230 results in a thinner hinge 230. With a thinner hinge 230, the force required to expose the needle 18 is reduced, thereby enhancing the tactiles of the protective sheath. However, even with a thinner hinge 230, the snap back of the protective arm 232 is not adversely affected due to the preload of hinge 230. The optimal thickness of the preloaded hinge 230 would be determined by tests comparing various pocket inclinations to various hinge thicknesses and their relative snap-back force and tactiles.

In FIG. 23, a modified coupling 243 is illustrated. The coupling 243 is illustrated with a pair of tabs or hooks 244 that snap together to couple the two halves of the protective arm together.

With reference once again to FIGS. 20 through 22, the sheath is illustrated with a modified connector body 122. The connector body 122 of this embodiment is semi-circular in cross-section as illustrated in FIG. 21. The connector body 122 is intended to be snap fit onto the syringe in the same manner as the connector body in each of the previous embodiments. By only using one-half of the connector body, the connector body of this embodiment reduces material costs and, in turn, reduces the cost of the sheath. Although it is intended that this connector body 122 can be snap fit onto the syringe, it may be necessary to add an adhesive between the connector body and the syringe to ensure that the connector body remains secured to the syringe during its movement between the opened and closed positions.

Referring now to FIGS. 24 to 28, a further embodiment of the sheath of the present invention is illustrated generally at 250. The sheath 250 is connected to a syringe 12 and includes a protective arm 252, a connector body 122, and a control finger 254. In FIG. 24, the sheath 250 is shown in bold lines in its normally closed position and in phantom lines in its open position.

With reference to FIG. 26, the slot 256 is shown at an angle to the longitudinal centerline of the needle 18, which is shown partially in phantom. In this embodiment, the angle of the slot 256 protects against inadvertent exposure of the needle 18. To expose the needle 18, the sheath 252 must be twisted with respect to the longitudinal center line of needle 18, as well as being rotated about an axis generally perpendicular to the longitudinal center line of the needle 18. This twisting and rotating action will result in the slot 256 being aligned with the needle 18 and allow the needle 18 to pass through the slot.

There is an additional advantage to the protective arm 252 having an angled slot 256. Due to the twisting and rotating action, the resilient hinge 258 is twisted, as well as being bent back, which provides greater biasing action to snap the protective arm 252 back to the normally closed position. Since the hinge 258 is resilient, it has a memory and snaps the protective arm back along the same path of travel that the protective arm 252 traveled from the normally closed position to the open position. In this way, the needle 18 can easily pass back through the slot 256 when the pressure on protective arm 252 is released.

To obtain the necessary twisting and rotating action, the disclosed embodiment shows the finger 254 angled with respect to a line generally perpendicular to the longitudinal center line of the needle 18. See FIG. 28. Due to the angle, as the finger is pulled back against the connector body 122, the protective arm 252 will be twisted and rotated. The degree of the angle will be determined by the angle of the slot with respect to the longitudinal center line of the needle 18.

In addition to the finger 254 being angled, the twisting action is also facilitated by the width and position of the resilient hinge 258 and the thickness of the hinge 258. The width and position can be selected such that the hinge is offset with respect to the longitudinal center line of the needle 18. As should be appreciated by those of ordinary skill in the art, with the hinge 258 being off center, the movement of the protective arm 252 will be forced into a twisting action. The location and width would be determined by trial and error depending upon the material and its thickness, as well as the angle of slot 256. Although not preferred, the twisting action could also be obtained by varying the thickness of the hinge 258.

Although the present invention has been described in detail with reference only to the presently preferred embodiments, it will be appreciated by those of ordinary skill in the art that various modifications can be made without departing from the invention. Accordingly, the invention is to be limited only by the following claims.

What is claimed is:

1. A shield for protecting the needle of a syringe, said syringe having a body portion and a needle, said shield comprising:

a connector for connecting the shield to the syringe;

at least one protective arm hinged to said connector;

biasing means normally biasing said arm to a closed position wherein said arm conceals said needle, said protective arm being manually displacable with respect to said syringe to an open position to expose said needle; said protective arm automatically traveling from the open position to the closed position and being unhindered throughout its travel from the open position to the closed position;

said protective arm and said connector being integrally formed as a one piece unit, with said biasing means being defined by a living hinge formed between said protective arm and said connector.

2. The shield of claim 1, further including a control grip extending outwardly from said protective arm, said control grip being adapted to be grasped by a user to manually displace said protective arm to expose said needle.

3. The shield of claim 2, wherein said control grip extends at approximately a 90 degree angle with respect to said protective arm.

4. The shield of claim 2, wherein said control grip includes a knurled surface to facilitate engagement by a user.

5. The shield of claim 1, wherein said protective arm is generally convex in cross-section.

6. The shield of claim 1, wherein said protective arm is generally tubular and has a longitudinally extending slot for receipt of said needle.

7. The shield of claim 6, wherein said longitudinally extending slot has a width which is slightly greater than the diameter of said needle such that said needle can move into and out off said protective arm through said slot.

8. The shield of claim 6, wherein said longitudinal slot of said protective arm includes a restrictive means restricting the egress of said needle from said protective arm.

9. The shield of claim 6, wherein said longitudinal slot of said protective arm includes a restrictive means for restricting the egress of said needle from said protective arm, said restrictive means providing relatively minimal restriction to the ingress of said needle into said protective arm.

10. The shield of claim 1, wherein said protective arm has integrally formed flaps defining a longitudinal slot for restricting the unintentional egress of said needle from said protective arm.

11. The shield of claim 1, wherein said protective arm is defined by a generally tubular wall and includes flaps which are integrally formed with said wall, said flaps having a reduced width relative to said wall to define a resilient hinge between said flaps and said wall, to permit the ingress and egress of said needle with respect to said protective arm.

12. The shield of claim 11, wherein said flaps are pre-stressed inwardly to provide greater resistance to the egress of said needle than the ingress of said needle.

13. The shield of claim 1, wherein said shield is formed in two longitudinal halves which are joined together.

14. The shield of claim 13, wherein said longitudinal halves are hinged together by a longitudinal hinge extending along one side such that said shield can be folded over said hinge.

15. The shield of claim 13, wherein one of said longitudinal halves includes a longitudinal slot extending the length of said one of said longitudinal halves.

16. The shield of claim 15, wherein said longitudinal halves include laterally extending slots between said connector and said protective arm.

17. The shield of claim 16, wherein one of said lateral slots extends through said respective side.

18. The shield of claim 1, wherein said protective arm has an end portion that covers the end of said needle.

19. The shield of claim 1, wherein said connector has a tapered cavity with a first and second opening, said first opening having a larger diameter than said second opening, such that said syringe can be inserted into said first opening and press fit along said taper.

20. The shield of claim 1, wherein said hinge includes a generally sinusoidal surface.

21. The shield of claim 1, further including a locking bar for locking the protective arm in said closed position;

said locking bar having a resilient hinge such that said locking bar can be folded against a bias as said protective arm is displaced with respect to said needle.

22. The shield of claim 1, wherein said protective arm includes a slot adapted to receive said needle:

said protective arm further including at least one biased flap partially closing said slot;

said biased flap resisting movement of said protective arm from said closed position with relatively little resistance against said protective arm moving to said normally closed position.

23. The shield of claim 1, wherein said protective arm includes a pocket for receipt of said needle.

24. The shield of claim 23, wherein said protective arm is angled with respect to the longitudinal center line of said needle.

25. The shield of claim 1, wherein said protective arm includes a longitudinally extending slot for the ingress and egress of said needle, said slot being angled with respect to the longitudinal centerline of said needle when said protective arm is in the closed position.

26. The shield of claim 25, wherein said protective arm includes a control grip extending outwardly from said protective arm, said control grip being adapted to be grasped by a user to manually displace said protective arm to expose said needle, said control grip being angled with respect to a line perpendicular to the longitudinal centerline of said needle such that movement of said control grip results in said protective arm twisting and rotating to expose said needle.

27. The shield of claim 25, wherein said living hinge is offset with respect to the longitudinal centerline of said needle.

28. A shield for protecting the needle of a syringe, said syringe comprising:

a connector for connecting the shield to the syringe;

at least one protective arm hinged to said connector, said protective arm being pivotable between first and second positions which define said protective arm's travel path, said first position being the normal position wherein said protective arm conceals said needle, said second position corresponding to said protective arm being pivotally displaced to expose said needle;

biasing means for automatically biasing said protective arm to said first position throughout the full extent of said travel path with said protective arm being unhindered throughout said travel path from said second position to said first position.

29. The shield of claim 28, further including a control grip extending outwardly from said protective arm, said control grip being adapted to be grasped by a user to manually displace said protective arm to expose said needle.

30. The shield of claim 28, wherein said protective arm and said connector are integrally formed.

31. The shield of claim 28, wherein said biasing means is defined by a notch formed between said protective arm and said connector to form a resilient hinge between said protective arm and said connector.

32. The shield of claim 29, wherein said control grip extends at approximately a 90-degree angle with respect to said protective arm.

33. The shield of claim 28, wherein said control grip includes a knurled surface to facilitate engagement by a user.

34. The shield of claim 28, wherein said biasing means is a resilient hinge interconnecting said arm to said connector.

35. The shield of claim 28, wherein said protective arm has sidewalls that extend about said needle when said protective arm is in said first position.

36. The shield of claim 28, wherein said protective arm has an end portion that covers the end of said needle.

37. The shield of claim 35, wherein said protective arm has integrally formed flaps defining a longitudinal slot which permits restricted egress of said needle from said protective arm and relatively unrestricted ingress.

38. The shield of claim 37, wherein said flaps are pre-stressed inwardly.

39. The shield of claim 28, further including a locking bar for locking the protective arm in said closed position;

said locking bar having a resilient hinge such that said bar articulates about said hinge;

said bar being adapted to fold against the bias of said resilient hinge as said protective arm is displaced with respect to said needle.

40. The shield of claim 28, wherein said protective arm includes a slot adapted to receive said needle;

said protective arm further including at least one biased flap partially closing said slot;

said biased flap resisting movement of said protective arm from said first position with relatively little resistance against said protective arm moving to said first position.

41. The shield of claim 40, wherein said needle engages said flap as said protective arm moves to or from said first position;

said flap providing greater relative resistance to said protective arm movement as said protective arm is moved from said first position.

42. The shield of claim 28, wherein said protective arm includes a pocket for receipt of said needle.

43. The shield of claim 42, wherein said protective arm is angled with respect to the longitudinal center line of said needle.

44. The shield of claim 28, wherein said protective arm includes a longitudinally extending slot for the ingress and egress of said needle, said slot being angled with respect to the longitudinal centerline of said needle when said protective arm is in the first position.

45. The shield of claim 28, wherein said protective arm includes a control grip extending outwardly from said protective arm, said control grip being adapted to be grasped by a user to manually displace said protective arm to expose said needle, said control grip being angled with respect to a line perpendicular to the longitudinal centerline of said needle such that movement of said control grip results in said protective arm twisting and rotating to expose said needle.

46. The shield of claim 28, wherein said living hinge is offset with respect to the longitudinal centerline of said needle.

47. A shield for protecting the needle of a syringe, said syringe having a body portion and a needle, said shield comprising:

a connector for connecting the shield to the syringe, said connector being generally annular and adapted to slip fit over the syringe;

at least one protective arm hingedly mounted upon said connector;

biasing means normally biasing said arm to a closed position wherein said arm conceals said needle, said protective arm being manually displaceable with respect to said syringe to expose said needle;

said protective arm and said connector being integrally formed as a one piece unit, with said biasing means being defined by a living hinge formed between said protective arm and said connector; and said shield being formed in two longitudinal halves which are joined together, said longitudinal halves being hinged together by a longitudinal hinge extending along one side such that said shield can be folded over said hinge.

48. The shield of claim 47, wherein one of said longitudinal halves includes a longitudinal slot extending the length of said one of said longitudinal halves.

49. The shield of claim 47, wherein said longitudinal halves include laterally extending slots between said connector and said protective arm.

50. The shield of claim 49, wherein one of said lateral slots extends through said respective side.

51. The shield of claim 47, wherein said protective arm is generally tubular and has a longitudinally extending slot for receipt of said needle, said longitudinally extending slot has a width which is slightly greater than the diameter of said needle such that said needle can move into and out of said protective arm through said slot.

52. The shield of claim 47, wherein said protective arm includes a slot adapted to receive said needle;

said protective arm further including at least one biased flap partially closing said slot;

said biased flap resisting movement of said protective arm from said closed position with relatively little resistance against said protective arm moving to said normally closed position.

* * * * *